United States Patent [19]

Seitzer

[11] 4,073,819
[45] Feb. 14, 1978

[54] 2,6-DIMETHYLNAPHTHALENE EXTRACTION PROCESS

[75] Inventor: Walter H. Seitzer, West Chester, Pa.

[73] Assignee: Sun Oil Company of Pennsylvania, Philadelphia, Pa.

[21] Appl. No.: 807,697

[22] Filed: June 17, 1977

[51] Int. Cl.$^2$ .............................................. C07C 7/01
[52] U.S. Cl. .............................................. 260/674 N
[58] Field of Search ................................... 260/674 N

[56] References Cited

U.S. PATENT DOCUMENTS

| | | | |
|---|---|---|---|
| 3,725,490 | 4/1973 | Nagahama et al. | 260/674 N |
| 3,812,198 | 5/1974 | Hedge | 260/674 N |

*Primary Examiner*—Delbert E. Gantz
*Assistant Examiner*—C. E. Spresser
*Attorney, Agent, or Firm*—J. Edward Hess; Donald R. Johnson; Stanford M. Back

[57] ABSTRACT

Extraction of 2,6-dimethylnaphthalene from isomeric mixtures containing the same by clathrate complex formation with m-nitrobenzoic acid may be significantly increased by first purifying the m-nitrobenzoic acid before forming the clathrate.

5 Claims, No Drawings

2,6-DIMETHYLNAPHTHALENE EXTRACTION PROCESS

BACKGROUND OF THE INVENTION

This invention relates to an improved process for the recovery of 2,6-dimethylnaphthalene. More particularly, this invention relates to an improved method for separating 2,6-dimethylnaphthalene (hereinafter "2,6-DMN") from hydrocarbon mixtures containing isomers of 2,6-DMN, e.g. 2,7-DMN; 1,7-DMN; 2,3-DMN, and the like by selectively forming a clathrate complex of 2,6-DMN with purified m-nitrobenzoic acid (hereinafter "m-NBA").

It is known from U.S. Pat. Nos. 3,725,490 and 3,812,198 that 2,6-DMN may be separated from mixtures containing its isomers, particularly 2,7-DMN, by first selectively forming a complex of 2,6-DMN with nitrobenzoic acid, separating the complex from the reaction mixture containing the DMN isomers, and then breaking the complex to yield a concentrated or purified 2,6-DMN. Conventionally, formation of the complex, particularly when the feed mixture only contains 2-3% 2,6-DMN, and room temperature is employed, is preceded by an induction period of up to 30 minutes or more, followed by sometimes longer periods of complex formation which yield only relatively small percentages of hydrocarbon.

SUMMARY OF THE INVENTION

It has now been found, in accordance with the present invention, that the period of complex formation, i.e. the complexing of m-nitrobenzoic acid with 2,6-dimethylnaphthalene from mixtures containing the same, can be substantially shortened, and the percentage concentration of said 2,6-DMN in the complex substantially increased relative to said shorter complexation period, if the m-nitrobenzoic acid is first pre-treated in a manner described in further detail hereinbelow.

DESCRIPTION OF THE INVENTION

Thus, it has been found that technical grade m-NBA which has first been recrystallized from a suitable organic solvent, such as xylene, tetralin or the like, or which has been recrystallized from water, followed by grinding to provide particle size crystals which will pass through a 40-mesh screen or less, results in a three to four-fold decrease in complexation time. In the former case, where recrystallization from e.g. xylene is employed, it has been found that even if small amounts of water are added to, or left in the crystals, the noted improvement in the rate of complex formation is not adversely affected, indicating that, advantageously, complete drying of the crystals is not necessary.

In a further embodiment it has been found that even commercially available pure m-NBA does not provide the noted improvement in complexation rate unless the acid crystals are first ground up to provide a crystal size of no more than about that which will pass through a 20-mesh sieve, thereby demonstrating that the size of the m-NBA crystal plays an important role in the noted rate improvement. However, as the data below will show, particle size alone does not provide the noted effect unless the m-NBA is first purified, i.e. the grinding of the unpurified, technical grade crystals does not itself result in any rate improvement.

It has also been discovered that for a particular charge stock, the amount of acid employed relative to the amount of hydrocarbon mixture containing the DMN isomers has an effect on the amount of 2,6-DMN removed from such mixtures. Thus, it has been found with a light catalytic gas oil that with acid loadings much above 6:1 with respect to the 2,6-DMN content, the 2,6-DMN is depleted, and the resulting complex contains lower amounts of the complexed oil. Desirably, then, the ratio of acid to this oil should be in the range of about 0.18 to 0.20 by weight and preferably 0.14 to 0.18.

The invention will now be illustrated by the following examples. In these examples, the hydrocarbon mixture containing the DMN's was a light catalytic gas oil (LCGO), boiling at 400°-600° F, and containing about 2.5% 2,6-DMN, together with such other DMN isomers as 2,7-, 1,6-, 2,3- and others.

The following desulfurized light catalytic gas oil charge stock is a typical feed:

55.5% lighter than 2-methyl naphthalene
  7.6% 2-methylnaphthalene
  2.6% 1- and 2-ethylnaphthalene
  2.5% 2,6-DMN
  2.3% 2,7-DMN
  10.2% 1,6-DMN
  2.3% 2,3-DMN
  16.5% heavier than DMN's

EXAMPLE 1

To 100 parts light catalytic gas oil (boiling 400°-600° F, 2.5% 2,6-DMN) was added 15 parts technical m-NBA which had been ground in a Waring blender to pass through a 40-mesh sieve. This mixture was stirred at room temperature and samples of the slurry were withdrawn periodically for analysis as follows:

| Time, min. | % Hydrocarbon in the solid |
| --- | --- |
| 5 | 1 |
| 15 | 1 |
| 30 | 2 |
| 45 | 10 |
| 60 | 19 |

The hydrocarbon in the final complex contained about 56% 2,6-DMN.

EXAMPLE 2

The m-NBA was recrystallized by heating 56 parts in 100 parts xylene to 120° C, cooling, filtering, washing with pentane and drying. When 15 parts of this purified material, all of which passed through a 40-mesh sieve, was reacted with 100 parts of gas oil, a rapid and more complete complexation occurred:

| Time, min. | % Hydrocarbon in the Solid |
| --- | --- |
| 5 | 17 |
| 10 | 24 |
| 15 | 24 |
| 30 | 26 |

The hydrocarbon contained 53% 2,6-DMN.

EXAMPLE 3

The m-NBA, as received, was recrystallized from water by heating 50 parts m-NBA in 50 parts water to 95° C, cooling, filtering, washing, and drying. These crystals had to be ground in the Waring blender to pass through 40-mesh sieve. Reacting 15 parts of this solid with 100 parts oil at room temperature gave the following:

| Time, min. | % Hydrocarbon in Complex | % 2,6 in Hydrocarbon |
|---|---|---|
| 5 | 4 | — |
| 15 | 22 | 58 |
| 30 | 25 | 59 |

The rapid reaction rate is important in that the complexing can be carried out countercurrently in a reactor of dimensions one-fourth or less of those required using impure m-NAB.

The following Table I summarizes the results obtained by additional runs carried out in accordance with the foregoing procedures, and includes comparative runs.

naphthalene with m-nitrobenzoic acid, followed by separation and breaking of the complex to recover said 2,6-dimethylnaphthalene in concentrated form, the improvement which comprises first recrystallizing the m-nitrobenzoic acid from water or a suitable organic solvent, if necessary followed by grinding the recrystallized acid before contacting it with said isomeric mixture.

2. The process according to claim 1 wherein the 2,6-dimethylnaphthalene is recovered from a light catalytic gas oil feedstock containing isomeric mixtures of dimethylnaphthalene and boiling in the range of about 400°–600° F.

3. The process according to claim 1 wherein the organic solvent is xylene.

4. The process according to claim 2 wherein the ratio of m-nitrobenzoic acid to 2,6 DMN content is in the range of 4 to 10.

TABLE I

RATE OF CLATHRATION IN LCGO AT ROOM TEMPERATURE
EFFECT OF PURITY OF mNBA

| | | | PRODUCT | | | |
|---|---|---|---|---|---|---|
| | | After 15 min. | | Complete Clathration | | |
| Treatment of mNBA[1] | gms mNBA/ 100 gms Oil | % oil | % 2,6 Clathrated | minutes | % oil | % 2,6[2] Clathrated |
| 1 Grind[3] | 20 | 1 | — | 60 | 19 | 105 |
| 2 Dry in vacuo at 40° C Grind [3] | 10 | 2 | — | 45 | 27 | — |
| 3 Recrystallize from Xylene | 15 | 24 | 99 | 10 | 24 | 99 |
| 4 Recrystallize from Water Grind[3] | 15 | 22 | 97 | 15 | 22 | 97 |
| 5 Recrystallize from Xylene | 10 | 24 | 68 | 10 | 24 | 68 |
| 6 Recrystallize from Xylene Add 5% H | 10 | 22 | — | 15 | 24 | — |
| 7 Pure Eastman as received | 10 | 19 | — | 30 | 26 | 66 |
| 8 Pure Eastman. Grind[3] | 10 | 26 | — | 15 | 26 | — |

[1]Eastman Technical Grade.
[2]Calculated assuming 2.5% 2,6-DMN in starting oil.
[3]Ground in blender (~ 3 minutes) to pass through 40 mesh sieve.

The invention claimed is:

1. In a process for the separation of 2,6-dimethylnaphthalene from isomeric mixtures containing the same by selective clathrate complexation of said 2,6-dimethyl- 5. The process according to claim 1 wherein the recrystallized acid is ground until its particle size will pass through at least a 20-mesh screen.

* * * * *